US006235953B1

(12) United States Patent
Schwarzmaier et al.

(10) Patent No.: US 6,235,953 B1
(45) Date of Patent: May 22, 2001

(54) PROCESS FOR PREPARING 1,2-DICHLOROETHANE BY DIRECT CHLORINATION

(75) Inventors: Peter Schwarzmaier, Kastl; Ingolf Mielke, Burgkirchen, both of (DE)

(73) Assignee: Vinnolit Monomer GmbH & Co. KG, Ismaning (DE)

( * ) Notice: Subject to any disclaimer, the term of this patent is extended or adjusted under 35 U.S.C. 154(b) by 0 days.

(21) Appl. No.: 09/214,181

(22) PCT Filed: Jun. 30, 1997

(86) PCT No.: PCT/EP97/03399

§ 371 Date: Aug. 23, 1999

§ 102(e) Date: Aug. 23, 1999

(87) PCT Pub. No.: WO98/01407

PCT Pub. Date: Jan. 15, 1998

(30) Foreign Application Priority Data

Jul. 4, 1996 (DE) ............................................ 196 26 827
Oct. 9, 1996 (DE) ............................................ 196 41 562

(51) Int. Cl.[7] ............................ C07C 17/02; F28D 21/00

(52) U.S. Cl. .......................... 570/246; 422/198; 422/208; 422/234

(58) Field of Search ............................ 570/246; 422/208, 422/198, 234

(56) References Cited

U.S. PATENT DOCUMENTS

| | | |
|---|---|---|
| 4,672,142 | 6/1987 | Hundeck et al. . |
| 4,774,373 | 9/1988 | Hundeck et al. . |
| 4,873,384 | 10/1989 | Wachi et al. . |
| 5,507,920 | 4/1996 | Schwarzmaier . |
| 5,610,144 | 3/1997 | Capet et al. . |

FOREIGN PATENT DOCUMENTS

| | | |
|---|---|---|
| 4029314 | 3/1992 | (DE) . |
| 4103281 | 3/1992 | (DE) . |
| 4133810 | 4/1993 | (DE) . |
| 4318609 | 7/1994 | (DE) . |
| 0075742 | 4/1983 | (EP) . |
| 0471987 | 2/1992 | (EP) . |
| 6901398 | 11/1969 | (NL) . |
| WO 93/01167 | 1/1993 | (WO) . |
| WO 93/12791 | 7/1993 | (WO) . |
| WO 94/15914 | 7/1994 | (WO) . |
| WO 94/15954 | 7/1994 | (WO) . |
| WO 94/15955 | 7/1994 | (WO) . |
| 94/17019 | 8/1994 | (WO) . |
| 96/03361 | 2/1996 | (WO) . |
| WO 96/38139 | 12/1996 | (WO) . |
| 91/6491 | 5/1992 | (ZA) . |
| 94/0535 | 10/1994 | (ZA) . |
| 95/6058 | 4/1996 | (ZA) . |

OTHER PUBLICATIONS

Lakhbir Singh et al., "Modulation of the in vivo actions of morphine by the mixed $CCK_{A/B}$ receptor antagonist PD 142898," *European Journal of Pharmacology,* vol.307, No. 3, 1996, pp. 283–289.

Bill W. Massey et al., "Effects of cholecystokinin antagonists on the discriminative stimulus effects of cocaine in rats and monkeys," *Drug and Alcohol Dependence,* vol. 34, No. 2, 1994, pp. 105–111.

J. Hughes et al., "Neuropeptides," *Arzneimittel–Forschung Drug Research,* vol. 42 (I), No. 2a, 1992, pp. 250–255.

A. Kuzmin et al., "Calcium Antagonists Isradipine and Nimodipine Suppress Cocaine and Morphine Intravenous Self–Administration in Drug–Naive Mice," *Pharmacology Biochemistry and Behavior,* vol. 41, 1992, pp. 497–500.

*Primary Examiner*—Alan Siegel
(74) *Attorney, Agent, or Firm*—Collard & Roe, P.C.

(57) ABSTRACT

The preparation of 1,2-dichloroethane (EDC) is carried out by feeding ethylene and chlorine into circulating EDC (direct chlorination) such that the reaction mixture boils and the heat of the reaction is led away from the gas space.

7 Claims, 3 Drawing Sheets

PROCESS FOR PREPARING 1,2-DICHLOROETHANE BY DIRECT CHLORINATION

This application is a 371 of PCT/EP97/03399 filed Jun. 30, 1997

BACKGROUND OF THE INVENTION

1. Field of the Invention

The invention relates to a process for preparing 1,2-dichloroethane by direct chlorination.

2. The Prior Art

The preparation of 1,2-dichloroethane (EDC below) by reacting ethylene with chlorine, which is generally referred to as direct chlorination, takes place with the liberation of heat of reaction. For better control of the reaction and for dissipating the heat of reaction it is common to use circulating liquid EDC. For this purpose liquid reaction mixture or crude EDC is taken off from the reaction chamber and the heat of reaction is utilized by way of a heat exchanger to operate distillation columns, for example. Such processes are known, for example, from EP-A-471 987 (ZA 91/6491), DE-A-4029314 and DE-A-41 33 810. From these documents it is also known that particularly intensive mixing of the reactants with the circulating EDC can be ensured by means of appropriate devices such as static mixers U.S. Pat. No. 4,873,384 describes a process for preparing EDC from ethylene and chlorine in liquid EDC in which the vapor of the reaction medium serves to recover some of the latent heat. U.S. Pat. No. 4,873,384 describes a process for preparing EDC from ethylene and chlorine in liquid EDC in which the vapor of the reaction medium serves to recover some of the latent heat.

SUMMARY OF THE INVENTION

The invention now relates to a process for preparing EDC by feeding ethylene and chlorine into circulating EDC with intensive mixing and heat recovery, which comprises carrying out the reaction at from 65 to 125° C. and at from 0.5 to 3.2 bar absolute, the pressure and temperature being chosen such that the reaction mixture boils, and conducting the heat of reaction away from the gas space and supplying it to a heat exchanger.

Figure 1:
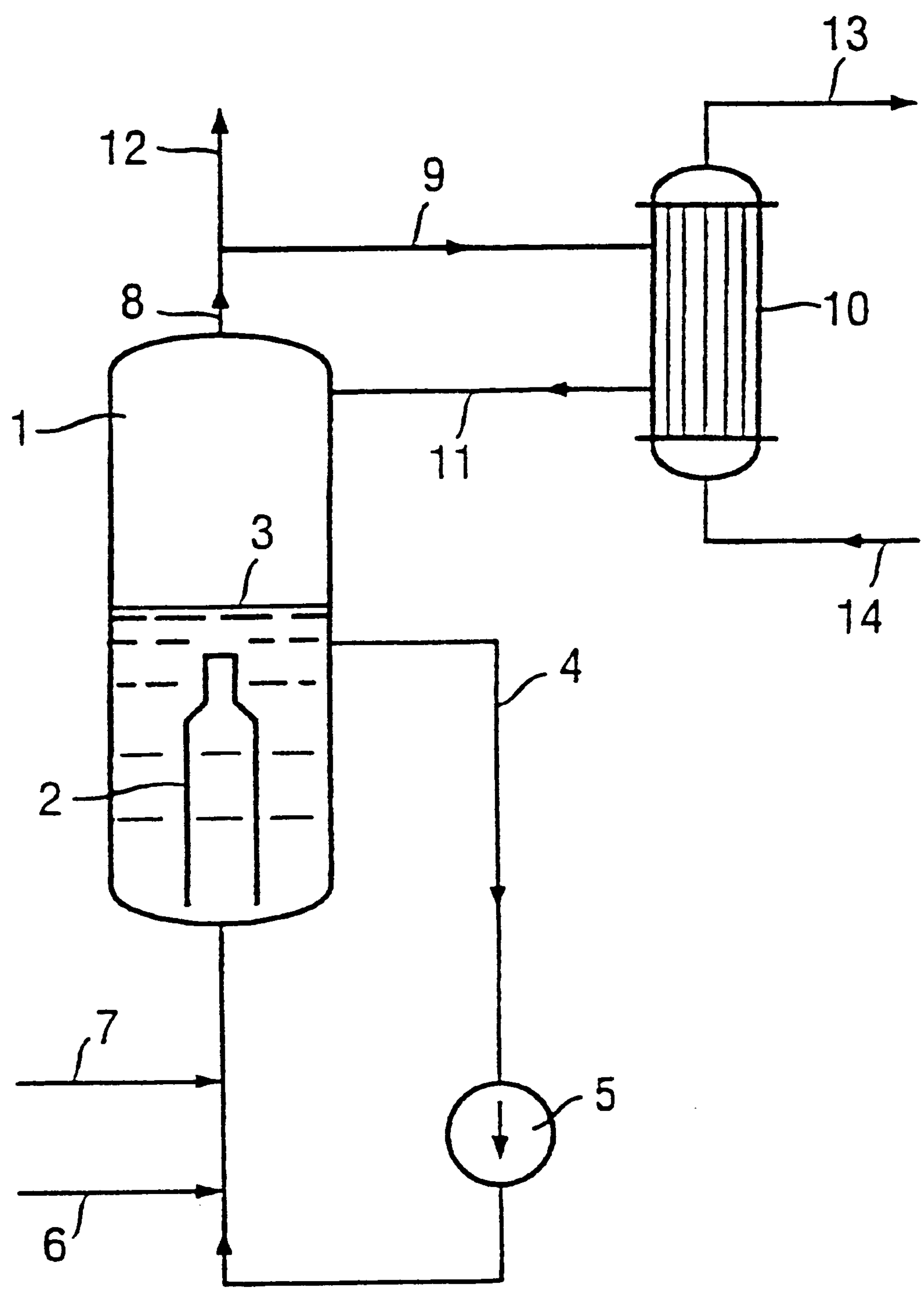
FIG. 1 shows an apparatus for carrying out the process of the invention.

The invention additionally relates to an apparatus for carrying out the process, which is shown diagrammatically in FIG. 1. In this figure the reference numbers have the following meanings:

1=Rector
2=Mixing device
3=Limit of the liquid EDC
4=Circulation line for liquid EDC
5=Pump
6=Infeed point for chlorine or ethylene
7=Infeed point for chlorine or ethylene
8=Offtake line for gaseous reaction mixture
9=Line to the heat exchanger 10
10=Heat exchanger
11=Return line from the heat exchanger 10 to the reactor 1
12=Line to the distillation column (not shown)
13=Line to or from the heat consumer unit
14=Line to or from the heat consumer unit

DETAILED DESCRIPTION OF PREFERRED EMBODIMENTS

Preferred embodiments of the novel process and of the apparatus are described in more detail below:

One process variant consists in taking off gaseous reaction mixture from the gas space, condensing the EDC in a heat exchanger and passing the liquid EDC back into the reactor.

Another embodiment of the invention consists in feeding the gaseous reaction mixture at the side into a distillation column from which inert gas fractions and unreacted ethylene are taken off from the top, pure EDC is taken off at the side below the infeed point, and high-boiling byproducts are separated off from the bottom. This distillation column can advantageously be operated with the heat of reaction from the gas space of the reactor. In this case the temperature in the lower part of the distillation column is somewhat lower than the temperature in the reaction chamber. It is, for example, 90° C. if the reaction is carried out at 105° C.

Figure 2:
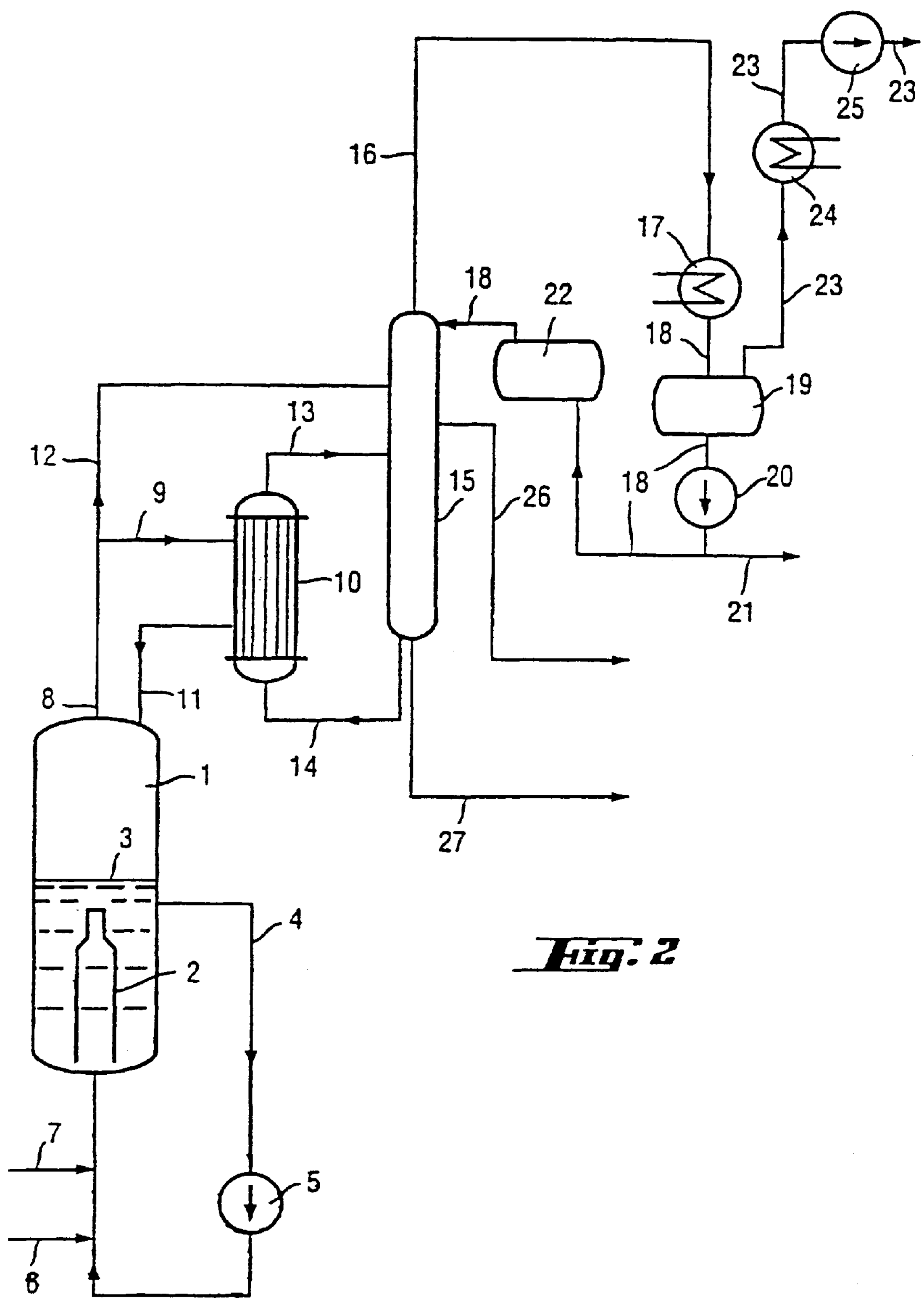
FIG. 2 shows another embodiment of the apparatus of the invention.

An appropriate apparatus for this embodiment of the invention is shown in FIG. 2. In this figure the reference numerals 1 to 14 have the meanings given above, and the others are:

15=Distillation column
16=Line for volatile products
17=Condenser
18=Circuit line
19=Return flow vessel
20=Pump
21=Line for taking off low-boiling products
22=Drier
23=Line for off-gas
24=Condenser
25=Pump
26=Line for EDC
27=Line for high-boiling products The volatile products pass from the head of the distillation column 15 through the line 16 and the condenser 17, by way of the circuit line 18, into the container 19 (return flow vessel). In addition, condensed liquid products pass via the circuit line 18 and a pump 20 into a drier 22, which prevents entrained water from becoming enriched in this circuit and causing corrosion. Via a line 21 it is possible to bring out low-boiling products separately.

Gaseous products, essentially unreacted ethylene and inert fractions, pass from the container 19 via a further condenser 24 and a pump 25 to the off-gas utilization unit.

The drier 22 can be of customary design and may function, for example, in accordance with known physical and/or chemical methods. If the drier 22 contains a drying agent, chemical drying agents such as phosphorus pentoxide or physical drying agents such as molecular sieves or silica gels are appropriate. Drying is advantageously effected as indicated in U.S. Pat. No. 5,507,920.

Figure 3:
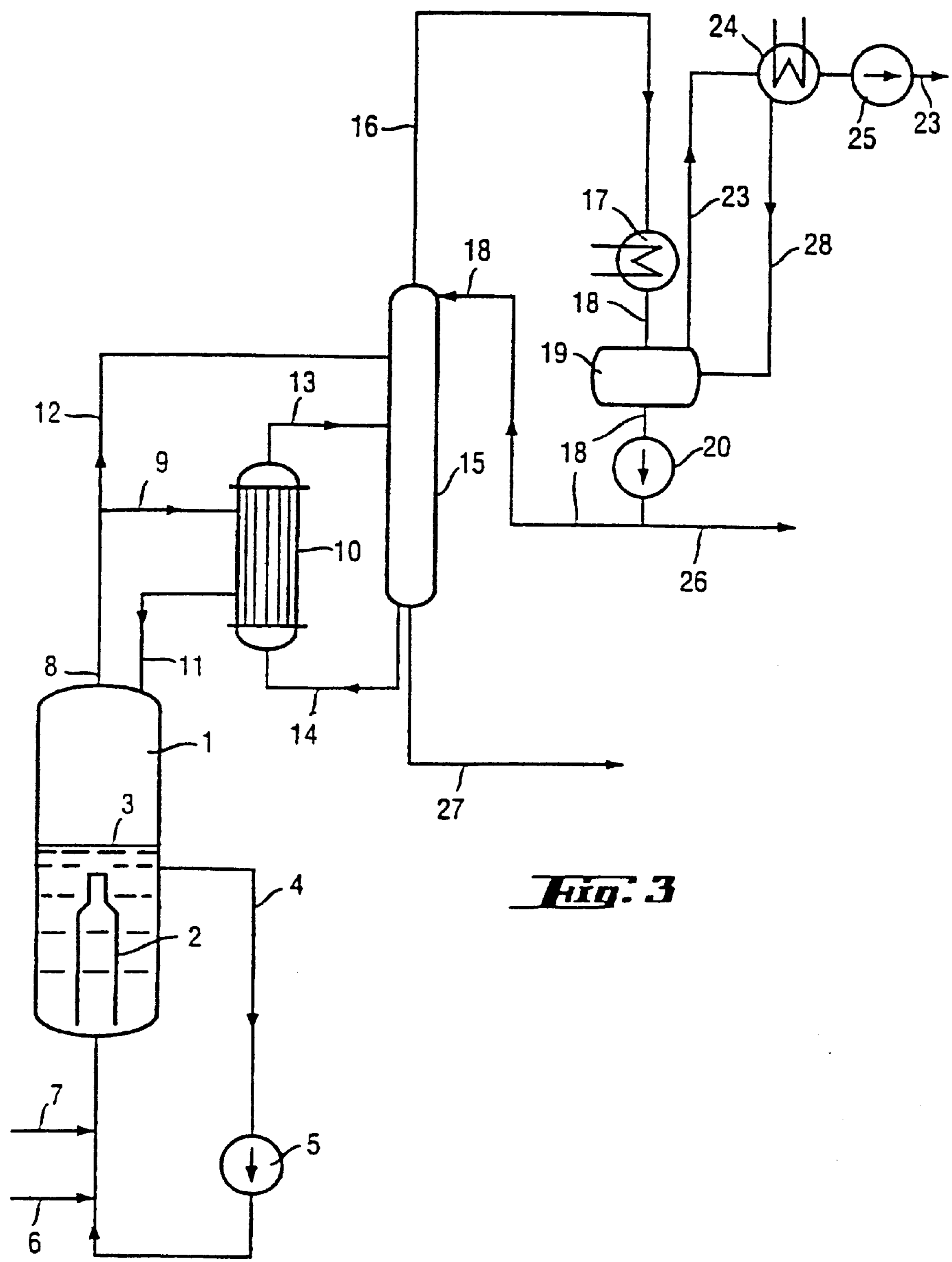
FIG. 3 shows a further embodiment of the apparatus of the invention.

In a different embodiment of the invention the distillation column is operated under reduced pressure. This embodiment is shown in FIG. 3. In this figure the reference numbers 1 to 21 (there is no drier 22) and 23 to 27 have the meanings given above and 28 is a return flow line from the condenser 24 to the container 19.

In this case the container 19 is under a more greatly reduced pressure than the column 15 (for example 0.8 bar absolute in the column 15, 0.26 bar absolute in the container 19). Pressure regulation here is by means of one or more pumps, for example the pump 25 (with appropriate valves, which are not shown in the figure). In this embodiment the products which arrive by way of the condenser 17 are depressurized in the container 19. The gas phase passes via the line 23 into the condenser 24, from which liquefied products flow back to the container 19 via the line 28. The liquid phase—pure EDC—is separated downstream of the pump 20 into the product stream (via line 26) and the return stream 18.

The process is carried out with the customary catalysts. Suitable catalysts are combinations of Lewis acids such as iron(III) chloride and halides of metals of the first or second subgroup of the Periodic Table of the Elements, especially sodium chloride, in a wide variety of molar ratios (NL-A-6901398, U.S. Pat. No. 4,774,373 or DE-A-41 03 281) and, in particular, with the catalyst system according to WO-A-94/17019 (ZA 94/0535), in which case during the entire reaction the molar ratio of sodium chloride to iron(III) chloride remains below 0.5, preferably in the range from 0.45 to 0.3. In this process the EDC is obtained in such high purity that particularly long standing times of the heat exchangers are achieved.

The novel implementation of the process entails a range of advantages:

The reaction can be carried out very safely and can be readily controlled at any time. By this means it is possible to keep the reaction temperature low, which suppresses the formation of byproducts. Owing to the fact that the heat of reaction is conducted away from the gaseous reaction mixture, the heat exchangers, for example circulation evaporators, can be given small dimensions, since the heat of condensation of the EDC is utilized as well. Another advantage is that the heat exchangers are not contaminated by entrained catalyst and high-boiling byproducts.

The utilization of the heat of reaction and heat of condensation is very effective and permits a large number of constructional designs of the process. The heat exchanger or exchangers can be arranged directly adjacent to the reactor, and the heat-utilizing apparatus can in turn also be built in the direct spatial vicinity of or around the heat exchanger or exchangers. By this means it is possible to avoid constructional expense and heat losses as a result of long lines and to save valuable space in the plant.

In the case of the abovementioned embodiments of the invention, in which inert gas fractions and unreacted ethylene are removed, the ethylene can be separated off from the inert fractions in a known manner and passed back to the process. Gas fractions such as oxygen or nitrogen are, for example, entrained by the chlorine, the oxygen here being regarded as inert as it is at a volume concentration below the explosion limit (3%). Off-gas recycling in the context of direct chlorination is described in WO-A-96/03361 (ZA 95/6058).

The implementation of the reaction is effected in a manner known per se, reference being made to the abovementioned documents in relation to this and to the details regarding apparatus.

The novel process is explained in more detail in the following examples.

EXAMPLE 1 (FIGS. 1 and 2)

In a direct chlorination reactor 1 with a static mixer 2, chlorine is fed in via the line 6 and ethylene is fed in via the line 7. The reactor is filled with liquid EDC to the liquid level 3 and this EDC is pumped in circulation via the line 4 and the pump 5. The gas mixture which emerges from the vapor space of the reactor via the line 8 (essentially comprising EDC but also traces of unreacted ethylene, oxygen, nitrogen and components which boil more readily than EDC) is predominantly (about 85% ) passed via the line 9 to a column heater 10 (heat exchanger), where it is condensed and passed back into the reactor 1 via the line 11. The energy of condensation is passed via the lines 13 and 14 to the distillation column 15 and is led away from the latter.

The smaller proportion of the gas mixture is fed via the line 12 into the distillation column 15 at the side, where unreacted ethylene, oxygen, nitrogen and traces of relatively low-boiling byproducts such as ethyl chloride and water are separated off at the top (line 16). The pure EDC is taken off from the column 15 via the line 26 (below the infeed point of the line 12).

Noncondensables such as ethylene, oxygen and nitrogen pass via the line 16, the condenser 17, the line 18, the container 19 and the line 23 to an off-gas condenser 24, and then to the compressor 25, which sends them under pressure to an off-gas utilization unit.

Condensables such as relatively low-boiling byproducts and an azeotropic mixture of EDC and water likewise pass first via the line 16, the condenser 17 and the circuit line 18 to the return flow vessel 19, but from there they pass via the conveying pump 20 to the drier 22, which prevents traces of entrained water from accumulating at the column head The dried condensate then flows via the circuit line 18 into the distillation column 15.

EXAMPLE 2 (FIG. 3)

The procedure of Example 1, first paragraph, is repeated, and then the procedure is as follows:

The smaller part of the gas mixture is fed via the line 12 into the distillation column 15. Pure EDC and unreacted ethylene, oxygen and nitrogen and traces of relatively low-boiling components pass via the line 16 to the EDC condenser 17 and then via the line 18 to the return flow vessel 19. A (single) vacuum pump 25 is used to establish a pressure of 0.8 bar absolute in the column 15 and 0.26 bar absolute in the return flow vessel 19, in order to separate off the unreacted ethylene dissolved in the EDC, and also the oxygen and nitrogen. Further EDC is condensed at +1° C. in the off-gas condenser 24, and the off-gas is passed via the line 23 to an off-gas utilization unit. Pure EDC from the return flow vessel 19 is passed via the line 26 to an EDC cracking furnace.

What is claimed is:

1. A process for preparing 1,2-dichloroethane (EDC) by feeding ethylene and chlorine into circulating EDC with intensive mixing and heat recovery, which comprises carrying out reaction in a reactor (1) at a temperature of from 65 to 125° C. and at a pressure of from 0.5 to 3.2 bar absolute, pressure and temperature being chosen such that a reaction mixture boils;

conducting heat of reaction away from a gas space and supplying said heat to at least one heat exchanger (10);

taking off part of the gaseous reaction mixture from the gas space, condensing the EDC in said heat exchanger (10) and passing the liquid EDC back to the reactor;

feeding a part (12) of the gaseous reaction mixture (8) at a side infeed point into a distillation column (15) from which inert gas fractions and unreacted ethylene (16)

are taken off from the top, pure EDC (26) is taken off at the side below the infeed point, and high-boiling by products (27) are separated off from the bottom; and providing from said distillation column (15) said line for volatile products (16) to a condenser (17) having a circuit line (18) to a return flow vessel (19) connected to a pump (20) having a line for taking off low-boiling products (21) and a drier (22) and there being a line for off-gas (23) leading to a condenser (24) and a pump (25).

2. The process as claimed in claim 1, wherein the distillation column is operated with the heat of reaction from the gas space of the reactor.

3. The process as claimed in claim 1, wherein the intensive mixing is effected if with a static mixer.

4. The process as claimed in claim 1, wherein the reaction is carried out with a catalyst system comprising a Lewis acid and a halide from the first or second group of the Periodic Table of the Elements.

5. The process as claimed in claim 4, wherein the catalyst employed comprises sodium chloride and iron(III) chloride in a molar ratio of below 0.5.

6. An apparatus for carrying out a process for preparing 1,2-dichloroethane (EDC) by feeding ethylene and chlorine into circulating EDC with intensive mixing and heat recovery, comprising a reactor (1), a mixing device (2), a limit of the liquid EDC (3), a circulation line for liquid EDC (4), a pump (5), infeed points for chlorine and ethylene respectively (6, 7), an offtake line for gaseous reaction mixture (8), a line (9) to a heat exchanger (10), a return line (11) from the heat exchanger (10) to the reactor (1), a line (12) to a distillation column (15) and lines (13, 14) to and from, respectively, the distillation column (15); and said distillation column (15) having a line for volatile products (16) leading to a condenser (17) and a circuit line (18) leading to a return flow vessel (19) and a Dump (20) having a line for taking off low-boiling Products (21) with a drier (22), a line for off-gas (23) leading to a condenser (24), a pump (25) with a line for EDC (26) and a line for high- boiling products (27).

7. The apparatus as claimed in claim 6, in which the drier (22) is omitted and a return flow line (28) from the condenser (24) to the container (19) is provided.

* * * * *